United States Patent
Dittmer et al.

(10) Patent No.: US 10,293,172 B2
(45) Date of Patent: May 21, 2019

(54) METHOD OF CONNECTING A WIRE TO A FEEDTHROUGH

(71) Applicant: Heraeus Deutschland GmbH & Co. KG, Hanau (DE)

(72) Inventors: Robert Dittmer, Hanau (DE); Senthil Kumar Balasubramanian, Singapore (SG); Leoni Wilhelm, Ober Ramstadt (DE); Thomas Schmitt, Krombach (DE); Thorsten Kaiser, Ortenberg (DE); Tim Asmus, Allendorf-Winnen (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 18 days.

(21) Appl. No.: 15/479,243

(22) Filed: Apr. 4, 2017

(65) Prior Publication Data

US 2017/0291033 A1 Oct. 12, 2017

(30) Foreign Application Priority Data

Apr. 7, 2016 (EP) .................................... 16164241

(51) Int. Cl.
| | | |
|---|---|---|
| *H05K 5/02* | (2006.01) | |
| *A61N 1/375* | (2006.01) | |
| *A61B 5/00* | (2006.01) | |
| *B23K 11/00* | (2006.01) | |
| *B23K 20/00* | (2006.01) | |
| *B23K 20/10* | (2006.01) | |
| *B23K 26/22* | (2006.01) | |

(Continued)

(52) U.S. Cl.
CPC ............ *A61N 1/3754* (2013.01); *A61B 5/686* (2013.01); *B23K 11/002* (2013.01); *B23K 20/004* (2013.01); *B23K 20/106* (2013.01); *B23K 26/22* (2013.01); *B23K 26/32* (2013.01); *H01B 1/02* (2013.01); *H01R 43/0207* (2013.01); *H05K 5/0091* (2013.01); *H05K 5/0247* (2013.01); *B23K 2101/42* (2018.08); *B23K 2103/16* (2018.08); *H01R 43/0214* (2013.01); *H01R 43/0221* (2013.01); *H01R 2201/12* (2013.01)

(58) Field of Classification Search
CPC ..................................................... H05K 5/0091
USPC ......................................................... 174/650
See application file for complete search history.

(56) References Cited

U.S. PATENT DOCUMENTS

| | | |
|---|---|---|
| 4,315,054 A | 2/1982 | Sack et al. |
| 4,678,868 A | 7/1987 | Kraska et al. |

(Continued)

FOREIGN PATENT DOCUMENTS

| | | |
|---|---|---|
| EP | 0877400 | 11/1998 |
| EP | 1685874 | 8/2006 |

(Continued)

*Primary Examiner* — Stanley Tso
(74) *Attorney, Agent, or Firm* — Dicke, Billig & Czaja, PLLC (57) ABSTRACT

One aspect relates to a feedthrough system. The feedthrough system includes a feedthrough and a wire. At least a portion of the feedthrough is made of an insulator and at least one area forming an electrically conductive cermet pathway. The cermet pathway may include an electrically conductive metal. The wire may be at least partially connected to the cermet pathway so that the material of the wire forms a joint microstructure with the electrically conductive material in the cermet pathway.

8 Claims, 4 Drawing Sheets

(51) Int. Cl.
   *H01B 1/02*    (2006.01)
   *H05K 5/00*    (2006.01)
   *B23K 26/32*   (2014.01)
   *H01R 43/02*   (2006.01)
   *B23K 101/42*  (2006.01)
   *B23K 103/16*  (2006.01)

(56) References Cited

U.S. PATENT DOCUMENTS

| | | |
|---|---|---|
| 4,987,035 A * | 1/1991 | Miller .................. C04B 37/026 |
| | | 403/272 |
| 6,999,818 B2 | 2/2006 | Stevenson et al. |
| 7,035,076 B1 | 4/2006 | Stevenson |
| 7,136,273 B2 | 11/2006 | Stevenson et al. |
| 7,145,076 B2 | 12/2006 | Knappen et al. |
| 7,174,219 B2 | 2/2007 | Wahlstrand et al. |
| 7,260,434 B1 | 8/2007 | Lim et al. |
| 7,274,963 B2 | 9/2007 | Spadgenske |
| 7,502,217 B2 | 3/2009 | Zhao et al. |
| 7,561,917 B2 | 7/2009 | Wegrzyn, III et al. |
| 7,564,674 B2 | 7/2009 | Frysz et al. |
| 7,706,124 B2 | 4/2010 | Zhao et al. |
| 7,720,538 B2 | 5/2010 | Janzig et al. |
| 7,736,191 B1 | 6/2010 | Sochor |
| 7,742,817 B2 | 6/2010 | Malinowski et al. |
| 7,761,165 B1 | 7/2010 | He et al. |
| 7,765,005 B2 | 7/2010 | Stevenson |
| 7,794,256 B1 | 9/2010 | Sochor |
| 2001/0013756 A1 | 8/2001 | Mori et al. |
| 2004/0116976 A1 | 6/2004 | Spadgenske |
| 2006/0012306 A1 * | 1/2006 | Bewlay .................. C22C 1/051 |
| | | 313/636 |
| 2006/0259093 A1 | 11/2006 | Stevenson et al. |
| 2007/0183118 A1 | 8/2007 | Fu et al. |
| 2008/0060834 A1 * | 3/2008 | Eck ...................... A61N 1/3754 |
| | | 174/152 GM |
| 2008/0119906 A1 | 5/2008 | Starke |
| 2008/0269831 A1 | 10/2008 | Erickson |
| 2010/0023086 A1 | 1/2010 | Lim |
| 2010/0258342 A1 | 10/2010 | Parker |
| 2012/0193125 A1 * | 8/2012 | Pavlovic .............. A61N 1/3754 |
| | | 174/152 GM |
| 2012/0193141 A1 | 8/2012 | Reisinger et al. |
| 2012/0197327 A1 * | 8/2012 | Specht ................ H01R 13/5224 |
| | | 607/5 |
| 2013/0299233 A1 * | 11/2013 | Troetzschel ............ A61F 2/02 |
| | | 174/650 |
| 2014/0345934 A1 * | 11/2014 | Markham ................ H02G 1/00 |
| | | 174/667 |
| 2017/0136245 A1 * | 5/2017 | Schibli .................. A61N 1/3756 |
| 2017/0291033 A1 * | 10/2017 | Dittmer ................. A61B 5/686 |

FOREIGN PATENT DOCUMENTS

| | | |
|---|---|---|
| EP | 1754511 | 2/2007 |
| WO | 03073450 | 9/2003 |
| WO | 2004110555 | 12/2004 |
| WO | 2008103166 | 8/2008 |
| WO | 2010091435 | 8/2010 |

* cited by examiner

Fig. 8

METHOD OF CONNECTING A WIRE TO A FEEDTHROUGH

CROSS-REFERENCE TO RELATED APPLICATIONS

This Utility Patent Application claims priority to European Patent Application No. EP 16164241.8, filed on Apr. 7, 2016, which is incorporated herein by reference.

BACKGROUND

One aspect relates to a method of connecting a wire to a feedthrough. Moreover, one aspect relates to a feedthrough system and an implantable medical device comprising such feedthrough system.

A multitude of electrical bushings providing electrical contact for various applications are known, examples including: U.S. Pat. Nos. 4,678,868, 7,564,674 B2, US 2008/0119906 A1, U.S. Pat. No. 7,145,076 B2, 7,561,917, US 2007/0183118 A1, U.S. Pat. Nos. 7,260,434B1, 7,761, 165, 7,742,817 B2, 7,736,191 B1, US 2006/0259093 A1, U.S. Pat. No. 7,274,963 B2, US 2004116976 A1, U.S. Pat. No. 7,794,256, US 2010/0023086 A1, U.S. Pat. Nos. 7,502, 217 B2, 7,706,124 B2, 6,999,818 B2, EP 1754511 A2, U.S. Pat. No. 7,035,076, EP 1685874 A1, WO 03/073450 A1, U.S. Pat. Nos. 7,136,273, 7,765,005, WO 2008/103166 A1, US 2008/0269831, U.S. Pat. No. 7,174,219 B2, WO 2004/110555 A1, U.S. Pat. No. 7,720,538 B2, WO 2010/091435, US 2010/0258342 A1, US 2001/0013756 A1, U.S. Pat. No. 4,315,054, and EP 0877400.

From US 2008/0119906 A1 is known a hermetically sealed electrical bushing for cardiac pacemakers and defibrillators. The bushing includes a flat ceramic disc that is used as an insulating support. The insulating disc includes openings, into which various electrodes are inserted as through-going contacts. Moreover, a metal flange is disclosed through which the ceramic disc can be connected to a housing.

From US 2012/0193141 A1 is known an electrical bushing for use in a housing of an implantable medical device, the bushing including at least one electrically insulating base body and at least one electrical conducting element. The electrical conducting element establishes, through the base body, at least one electrically conductive connection between an internal space of the housing and an external space. The conducting element is hermetically sealed with respect to the base body.

Electrical bushings generally serve to establish an electrical connection between a hermetically sealed interior and an exterior of the therapeutic device. Known implantable therapeutic devices are cardiac pacemakers or defibrillators, which usually include a hermetically sealed metal housing which is provided with a connection body, also called header, on one of its sides. The connection body includes a hollow space having at least one connection socket or plug socket for connecting electrode leads. In this context, the connection socket includes electrical contacts in order to electrically connect the electrode leads to the control electronics on the interior of the housing of the implantable therapeutic device. Usually, hermetic sealing with respect to a surrounding is an essential prerequisite of an electrical bushing of this type. Therefore, lead wires that are introduced into an electrically insulating base body (also called signal-transmission elements) through which the electrical signals are propagated, must be introduced into the base body, usually such as to be free of gaps.

Conventionally, a connection between such electrode or electric wire and a conductive pathway through the insulating base body is done by means of a bond pad. The application of such bond pad is done by PVD, CVD, sputtering and the like and is therefore rather costly and time consuming. This is all the more, if additionally a masking of the surrounding surfaces is necessary.

For these and other reasons, a need exists for the present invention.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Further measures and advantages of the embodiments are evident from the claims, the description provided hereinafter, and the drawings. The embodiments are illustrated through several examples in the drawings. In this context, equal or functionally equal or functionally corresponding elements are identified through the same reference numbers. The invention shall not be limited to the exemplary embodiments.

DETAILED DESCRIPTION

In the following Detailed Description, reference is made to the accompanying drawings, which form a part hereof, and in which is includes by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

One embodiment provides a method of connecting a wire to a feedthrough, a feedthrough system with such feedthrough, and an implantable medical device comprising such feedthrough system, whereby the feedthrough system solves or at least mitigates the above mentioned problems. Refinements of the embodiments, which can be implemented alone or in combination, are specified in the dependent claims.

Embodiments of the method of connecting a wire to a feedthrough include the following steps, not necessarily in this order:

providing a feedthrough comprising an insulator and an electrically conductive cermet pathway, and wherein the cermet pathway includes an electrically conductive metallic material, providing a wire made of an electrically conductive material, arranging an end of the wire in at least partial contact with the cermet pathway, and generating a joint microstructure comprising the material of the cermet pathway and the material of the wire.

In general, a feedthrough system in accordance with one embodiment includes a feedthrough and a wire. The wire may have above mentioned (first) end for the connection to the cermet pathway and another (second) end for a connection to an electrode, a metallic conductor, another wire, a ribbon, a lead or the like. This second end of the wire may be connected to any kind of electrical connector or device that connects for example, to an electrode that stimulates a respective body part.

At least a portion of the feedthrough may be made of an insulating matrix with at least one area forming the electrically conductive pathway, that is, forming an electrically conductive passage through a thickness of the feedthrough. The term "insulating matrix" can be understood as a ceramic matrix with a minor amount of additives. In this insulating matrix, the electrically conductive pathways may be embedded. Such pathway may form an electrically conductive matrix, which can here be understood as a metal matrix with a minor amount of ceramic. The electrically conductive matrix in the area of the pathway may include an electrically conductive metal. It will be understood that the pathway may be surrounded by the isolating matrix. The wire may be arranged between the electrode and the cermet pathway and the wire is connected to the cermet pathway so that the material of the wire forms a joint or bonded microstructure with the electrically conductive material in the cermet pathway. The feedthrough system in accordance with one embodiment may be part of an implantable medical device further comprising an electric and/or electronic device arranged at least partially in contact with the feedthrough system.

So in contrast to a conventional bonding between the conductive pathway of the feedthrough and the wire by means of a bond pad, the bond pad can be omitted. Therefore, also a masking of surrounding surfaces can be omitted. As a result, the number of components and manufacturing steps for a feedthrough system may be reduced. At the same time, the stability of the feedthrough system can be maintained. In other words, a sufficiently stable and electrically conductive connection between the feedthrough and the wire can be achieved despite a rather low metal content of the cermet forming the conductive pathway.

The wire is connected to the pathway so that the material of the wire forms a joint microstructure with the electrically conductive material in the pathway.

According to an embodiment, the joint microstructure of the material of the wire and the electrically conductive material in the pathway is formed by heat. Thereby usually the two or more materials comprised in the joint microstructure are at least partially mixed. Hence, in case of the "joint microstructure comprising the material of the cermet pathway and the material of the wire", the material of the cermet pathway and the material of the wire are at least partially mixed with each other. Usually, a further material such as a solder, etc. is not present in the joint microstructure according to this embodiment.

That heat may be generated for example by pressure and ultrasonic vibration, by a laser and/or by resistance welding.

According to an embodiment may the pressure and ultrasound vibration be provided by sonotrode with a wire bonding tool (capillary) having a pointed tip. The pointed tip has a small contact surface and thus allows for a contact of only the wire end portion on the pathway. It will be understood that small but very fast movements back and forth will cause a heating of the wire material and the pathway material due to friction between these materials. Together with the pressure, the friction can be large enough to at least partially melt both materials together. To the pressure and ultrasound vibration, a heating to for example, about 150° C. by means of a heating stage can be added.

According to another embodiment may the material of the pathway be pre-conditioned or pre-heated by a laser. In other words, the pathway is firstly heated by the laser so as to partially melt both the platinum (for example) and the ceramic in the pathway, yielding a phase separation. In this process, a platinum-rich top layer is created that facilitates the subsequent laser welding, especially in a pathway with low metal content. This pre-shot must be strong enough to yield a platinum-enriched surface layer but not so strong that a thick ceramic layer underneath is formed. After having stopped the pre-heating, the end of the wire may be arranged in contact with the pathway and the joint microstructure may be generated by further heat provided by the laser.

According to an embodiment may the joint microstructure be generated by two electrodes of a resistance welding tool being arranged along the length of the wire and on the pathway. Using a miniaturized tool, it is possible to place both poles/electrodes of the tool next to each other on top of the wire and of the pathway. By doing so, the current can enter the pathway through the first pole/electrode, flow through the wire and pathway and exits through the second pole or electrode. Thus, two welding spots are created, forming a strong bonding.

According to another embodiment may the joint microstructure be generated by a resistance welding tool, wherein a first pole or electrode is arranged on the wire and wherein a second pole or electrode of the resistance welding tool is arranged on an opposite site of the pathway, so that the current may enter the first pole/electrode, flow from the wire into the pathway and exits the pathway through the second pole or electrode.

The matrix of the material in the at least one area forming an electrically conductive pathway may include in accordance with an embodiment 30 to 90 percent by volume of a metallic component out of the group consisting of platinum, a platinum alloy, iridium, niobium, molybdenum, titanium, a titanium alloy, cobalt, zirconium, chromium, tantalum, a tantalum alloy, tungsten, a tungsten alloy. Furthermore, the matrix of the pathway includes at least one ceramic component selected from the group consisting of: aluminum oxide, for example, $Al_2O_3$; zirconium oxide, for example, $ZrO_2$; magnesium oxide, for example, MgO; ZTA; ATZ; Y-TZP; aluminum nitride; aluminum titanate; a piezoceramic material, for example, a lead-free piezoceramic material selected from the group consisting of $Ba(Zr, Ti)O_3$, $Ba(Ce, Ti)O_3$, KNN, KNN—$LiSbO_3$, and KNN—$LiTaO_3$.

According to an embodiment, the wire includes a metallic material out of the group consisting of gold, copper, aluminum, palladium, silver, platinum, a platinum alloy, iridium, niobium, molybdenum, titanium, a titanium alloy, tantalum, a tantalum alloy, tungsten, a tungsten alloy, stainless steel, a cobalt-chromium alloy. In other words, the wire may be made of gold, silver, copper, aluminum, alloyed copper, alloyed gold, alloyed silver, palladium coated copper, gold coated silver; welding between these metallic materials results in the formation of disordered or ordered alloys by means of diffusion. The wire may also be made in form of clad wires, which means with a metal A in a core of the wire and a different metal B on a surface of the wire.

The wire may have any cross section and shape suitable for an electrical connection.

This can, for example, be a wire with a circular, oval, square or rectangular cross section, a flat, elongated ribbon or a thin metal plate with a complex external shape.

According to another embodiment, wherein the area forming the electrically conductive pathway has a cross-section or diameter of up to 5 mm. It will be understood that a small cross section of the pathway allows for an arrangement of a plurality of pathways close to each other so that different leads of a wire may be connected to corresponding pathways without spreading the wire leads unnecessarily.

According to another embodiment, the connection between a wire and a pathway illustrates a tensile strength between 200 MPa and 2000 MPa. According to another embodiment, the connection between a wire and a pathway illustrates a tensile strength between 500 MPa and 1500 MPa.

In the following, definitions are provided of terms as they will be used herein.

The term implant encompasses an (active) implantable medical device and shall include any device which is set up to perform at least one medical function and which can be introduced into a body tissue of a human or animal user. As a general rule, the medical function can include any function selected from the group consisting of a therapeutic function, a diagnostic function, and a surgical function. For example, the medical function can include at least one actuator function, in which an actuator is used to exert at least one stimulus on the body tissue, for example, an electrical stimulus.

All implants can usually include, for example, at least one housing, for example, at least one hermetically sealed housing. The housing can in one embodiment enclose at least one electronics unit, for example a triggering and/or analytical electronics unit of the implant.

The term active implantable medical device (also called AIMD) shall include all implantable medical devices that can conduct electrical signals from a hermetically sealed housing to a part of the body tissue of the user and/or receive electrical signals from the part of the body tissue of the user. Accordingly, the term, active implantable medical device, includes, for example, cardiac pacemakers, cochlea implants, implantable cardioverters/defibrillators, nerve, brain, organ or muscle stimulators as well as implantable monitoring devices, hearing aids, retinal implants, muscle stimulators, implantable drug pumps, artificial hearts, bone growth stimulators, prostate implants, stomach implants or the like.

A housing of an implant shall be understood to be an element that encloses, at least in part, at least one functional element of the implantable medical device that is set up to perform the at least one medical function or promotes the medical function. For example, the housing includes at least one internal space that takes up the functional element fully or in part. For example, the housing can be set up to provide mechanical protection to the functional element from stresses occurring during operation and/or handling, and/or protection to the functional element from influences of its surroundings such as, for example, influences of a body fluid. The housing can, for example, border and/or close the implant with respect to the outside.

The housing may be provided to be hermetically sealed such that, for example, the internal space is hermetically sealed with respect to the external space. In this context, the term, "hermetically sealed", can illustrate that moisture and/or gases cannot permeate through the hermetically sealed element at all or only to a minimal extent upon the intended use for the common periods of time (for example 5-10 years). The so-called leak rate, which can be determined, for example, by leak tests, is a physical parameter that can describe, for example, a permeation of gases and/or moisture through a device, for example, through the electrical bushing and/or the housing. Pertinent leak tests can be carried out with helium leak testers and/or mass spectrometers and are specified in the Mil-STD-883G Method 1014 standard. In this context, the maximal permissible helium leak rate is determined as a function of the internal volume of the device to be tested. According to the methods specified in MIL-STD-883G, method 1014, section 3.1 and taking into consideration the volumes and cavities of the devices to be tested that are used in the application of one embodiment, the maximal permissible helium leak rates can, for example, be from $1\times10^{-8}$ atm*$cm^3$/sec to $1\times10^{-7}$ atm*$cm^3$/sec.

The term, "hermetically sealed", shall be understood, for example, to mean that the device to be tested (for example the housing and/or the electrical bushing and/or the housing with the electrical bushing) has a helium leak rate of less than $1\times10^{-7}$ atm*$cm^3$/sec. In one embodiment, the helium leak rate can be less than $1\times10^{-8}$ atm*$cm^3$/sec, in one embodiment, less than $1\times10^{-9}$ atm*$cm^3$/sec. For the purpose of standardization, the above-mentioned helium leak rates can also be converted into the equivalent standard air leak rate. The definition of the equivalent standard air leak rate and the conversion are specified in the ISO 3530 standard.

For example, a pathway element may be hermetically sealed with respect to the isolator, at least in part. In this context, hermetic sealing shall be understood to mean a sealing, which in one embodiment is designed to be hermetically sealed, in one embodiment as such and without any contribution of further elements, whereby reference shall be made to the definition provided above with regard to the term, "hermetically sealed". However, in addition, the term, "hermetically sealed, at least in part" can include refinements, in which the pathway element is hermetically sealed with respect to the electrically insulating isolator involving a contribution of one or more further element(s).

Furthermore, the isolator is provided to be electrically insulating. This means that the isolator, fully or at least regions thereof, is made from at least one electrically insulating material. In this context, an electrically insulating material shall be understood to mean a material with a resistivity of at least $10^7$ Ohm*m, in one embodiment, of at least $10^8$ Ohm*m, in one embodiment of at least $10^9$ Ohm*m, and in one embodiment of at least $10^{11}$ Ohm*m. For example, the isolator can be provided such that, as mentioned above, a flow of current between a conducting element and the housing and/or between multiple conducting elements is prevented, at least largely, for example through the resistivity values between the conducting element and the housing as specified above being implemented. For example, the isolator can include at least one ceramic material. The isolator may include magnesium oxide (MgO), silicon oxide (Sift) or glass.

In this context, the pathway shall be understood as a conducting element or electrical conducting element which generally means an element set up to establish an electrical connection between at least two sites and/or at least two elements. For example, the conducting element can include one or more electrical conductors, for example metallic conductors. In the scope of one embodiment, the conducting element is made fully or partly of at least one cermet pathway, as mentioned above.

The isolator can, for example, be made fully or partly from one or more sinterable materials, for example, from one or more ceramic-based sinterable materials. The conducting element or elements can fully or partly be made of one or more cermet-based sinterable materials. Moreover, the at least one conducting element can also, as mentioned above, include one or more additional conductors, for example one or more metallic conductors with no ceramic fraction.

The term "cermet" shall refer to a composite material made of one or more ceramic materials in at least one metallic matrix or a composite material made of one or more metallic materials in at least one ceramic matrix. For production of a cermet, for example, a mixture of at least one ceramic powder and at least one metallic powder can be used to which, for example, at least one binding agent and, if applicable, at least one solvent can be added. The ceramic powder or powders of the cermet in one embodiment have a mean grain size of less than 10 µm, in one embodiment less than 5 µm, and in one embodiment less than 3 µm. The metallic powder or powders of the cermet in one embodiment have a mean grain size of less than 15 µm, in one embodiment less than 10 µm, and in one embodiment less than 5 µm. For production of an isolator, for example, at least one ceramic powder can be used to which, for example, at least one binding agent and, if applicable, at least one solvent can be added. In this context, the ceramic powder or powders in one embodiment has/have a mean grain size of less than 10 µm (1 µm is equal to $1 \times 10^{-6}$ m), in one embodiment less than 5 µm, in one embodiment less than 3 µm. For example, the median value or the d50 value of the grain size distribution is considered to be the mean grain size in this context. The d50 value corresponds to the value at which 50 percent of the grains of the ceramic powder and/or metallic powder are finer and 50 percent are coarser than the d50 value.

A ceramic manufacturing method shall be understood to mean a procedure that includes at least one sintering process of at least one insulating and/or at least one cermet material. As shall be explained in more detail below, the ceramic manufacturing method can, for example, include a forming for the manufacture of at least one form body, for example one ceramic green compact and/or at least one ceramic brown compact.

A sintering or a sintering process shall generally be understood to mean a procedure for the manufacture of materials or work-pieces, in which powdered, for example, fine-grained, ceramic and/or metallic substances are heated and connected in the process. This process can proceed without applying external pressure onto the substance to be heated or can, for example, proceed under elevated pressure onto the substance to be heated, for example under a pressure of at least 2 bar, in one embodiment higher pressures, for example pressures of at least 10 bar, for example, at least 100 bar, or even at least 1000 bar. The process can proceed, for example, fully or partly, at temperatures below the melting temperature of the powdered materials, for example at temperatures of 700 degrees centigrade to 1700 degrees centigrade. The process can be carried out, for example, fully or partly, in a tool and/or a mold such that a forming step can be associated with the sintering process. Aside from the powdered materials, a starting material for the sintering process can include further materials, for example one or more binding agents and/or one or more solvents. The sintering process can proceed in one or more steps, whereby additional steps can precede the sintering process, for example one or more forming steps and/or one or more debinding steps.

The sintering process, for example, of the cermet, but of the isolator just as well, for example, can proceed comparable to a sintering process that is commonly used for homogeneous powders. For example, the material can be compacted in the sintering process at high temperature and, if applicable, high pressure such that the cermet is virtually sealed tight or has no more than closed porosity. Usually, cermets are characterized by their particularly high toughness and wear resistance. Compared to sintered hard metals, a cermet-containing transmission element usually has a higher thermal shock and oxidation resistance and usually a thermal expansion coefficient that is matched to a surrounding insulator.

For the pathway according to one embodiment, the at least one ceramic component of the cermet can include, for example, at least one of the following materials: glass in general, aluminum oxide ($Al_2O_3$), magnesium oxide (MgO), silicon oxide ($SiO_2$), zirconium dioxide ($ZrO_2$), zirconium oxide-toughened aluminum oxide (ZTA-Zirconia Toughened Aluminum-$Al_2O_3/ZrO_2$), yttrium-toughened zirconium oxide (Y-TZP), aluminum nitride (AlN), magnesium oxide (MgO), piezoceramic materials, barium(Zr, Ti) oxide, barium(CE, Ti) oxide, and sodium-potassium-niobate.

For the pathway according to one embodiment, the at least one metallic component of the cermet can include, for example, at least one of the following metals and/or an alloy based on at least one of the following metals: platinum, iridium, niobium, molybdenum, tantalum, a tantalum alloy, tungsten, a tungsten alloy, titanium, cobalt, chromium, zirconium.

An electrically conductive connection is usually established in the cermet pathway when the metal content exceeds the so-called percolation threshold at which the metal particles in the sintered cermet are connected to each other, at least in spots, such that electrical conduction is enabled. For this purpose, experience tells that the metal content should be 25 percent by volume and more, in one embodiment 32 percent by volume, in one embodiment more than 38 percent by volume, depending on which materials have been selected. The metal content can, for example, be 25 percent by volume to 90 percent by volume, in one embodiment 32 percent by volume to 60 percent by volume, and in one embodiment 38 percent by volume to 50 percent by volume. The electrically conductive connection may also depend on a constitution of the material, as for example, grain size, grain shape, and grain distribution.

In the scope of one embodiment, the terms, "including a cermet," "comprising a cermet," and "cermet-containing", are used synonymously. Accordingly, the terms refer to the property of an element, being that the element contains cermet. This meaning also includes the variant of an embodiment in that the element, for example the pathway element, consists of a cermet, that is, is fully made of a cermet.

Finally, the term "electrode" as used herein shall be understood as an electrical element which may be active or passive, that is, which may supply electrical current in the form of pulses or continuously to for example a tissue in a human or animal body, or which may be suitable to measure a parameter like a sensor, wherein the parameter may for example be a temperature, a pressure, a movement, a chemical value like a pH-value or a presence of a specific chemical component. As described above with respect to various implantable medical device, the electrode shall indicate an element suitable to achieve the intended medical function of the implant.

Figure 1:
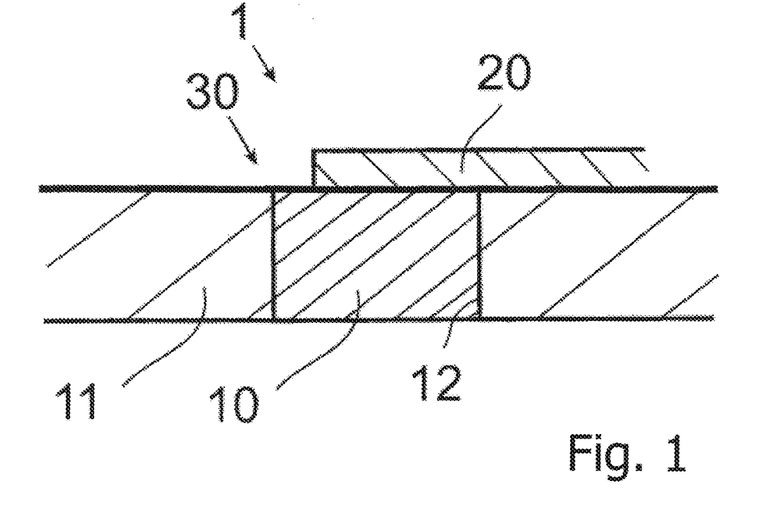
FIG. 1 illustrates a wire in contact with a pathway.

FIG. 1 is a sectional view showing a feedthrough system 1 comprising a wire 20 and a feedthrough 30 comprising a pathway 10 and an isolator 11. The wire 20 is in partial contact with an outer surface of the area forming the pathway 10. It is noted that FIG. 1 may be understood as a starting situation of a method of connecting for example an electrode, here the wire 20 coming from that electrode, with the pathway 10. Therefore, the wire is not yet fixedly connected to the pathway in FIG. 1. The feedthrough system 1 may be part of an implantable medical device further comprising an electric and/or electronic device arranged at least partially in contact with the feedthrough system 1. This contact may be a direct, physical connection and/or a rather indirect, electrical contact through for example, an electrical conductor, for example in form of wires, solder, etc.

In FIGS. 1 to 6, the hatching of the pathway 10 and the feedthrough 30 are oriented in the same direction, with the hatching of the pathway 10 being closer than that of the feedthrough 30. This shall indicate that the pathway 10 and the feedthrough 30 may include one or more components which are or can be manufactured in a sintering procedure, or the pathway 10 and the feedthrough 30 are or may both be manufactured in a sintering procedure. For example, the pathway 10 and the feedthrough 30 are or may be manufactured in a co-sintering procedure, that is, a procedure of simultaneous sintering of these elements. For example, the pathway 10 and the feedthrough 30 each may include one or more ceramic components that are manufactured, and in one embodiment compacted, in the scope of at least one sintering procedure.

As the pathway 10 also includes an electrically conductive metallic material, a transition within the joint microstructure between the pathway 10 and the isolator 11 may occur. Line 12 in FIG. 1 shall indicate such a transition. It is noted that a pathway 10 according to any one of the described embodiments, may be flush with a surface of the feedthrough 30, as illustrated. However, the pathway 10 may also project beyond the surface, for example, into the internal space and/or the external space of the feedthrough 30.

Figure 2:
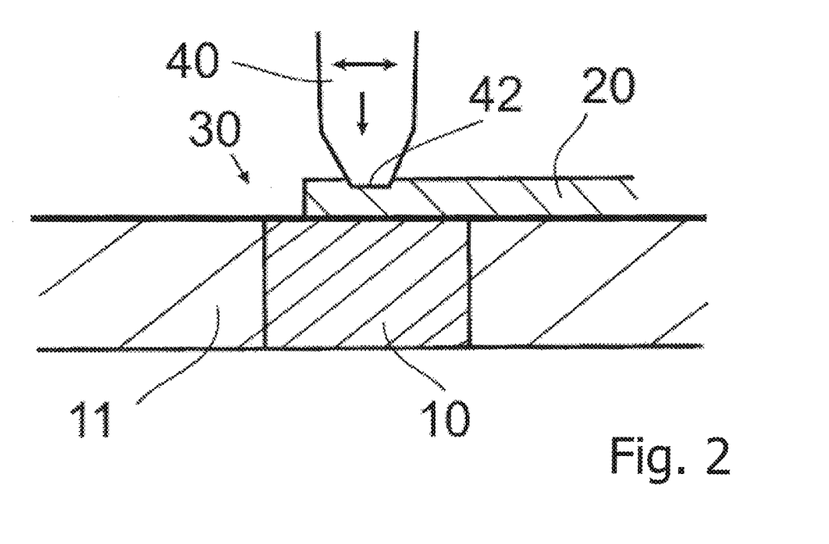
FIG. 2 illustrates an embodiment of connecting a wire to a pathway.

FIG. 2 illustrates a first way of generating a joint microstructure including the material of the wire 20 and the material of the pathway 10. To achieve such a joint microstructure, heat is generated at the contact surface of the pathway 10 and the wire 20. In accordance with the embodiment of FIG. 2, an ultrasound sonotrode 40 is pressed from above onto the wire 20. The wire 20 may also be fed from top to bottom instead of the shown lateral approach. The end face 42 of the sonotrode is in contact with the wire and the sonotrode vibrates with a side movement, as indicated by the double arrow in FIG. 2. Such a fast side movement causes the wire to vibrate relative to the pathway 10 so that the friction between the wire and the pathway 10 causes a heat which is high enough to partially and superficially melt the metallic material in the pathway 10 as well as the material of the wire 20. Heat can additionally be applied by an external heater.

Figure 3:
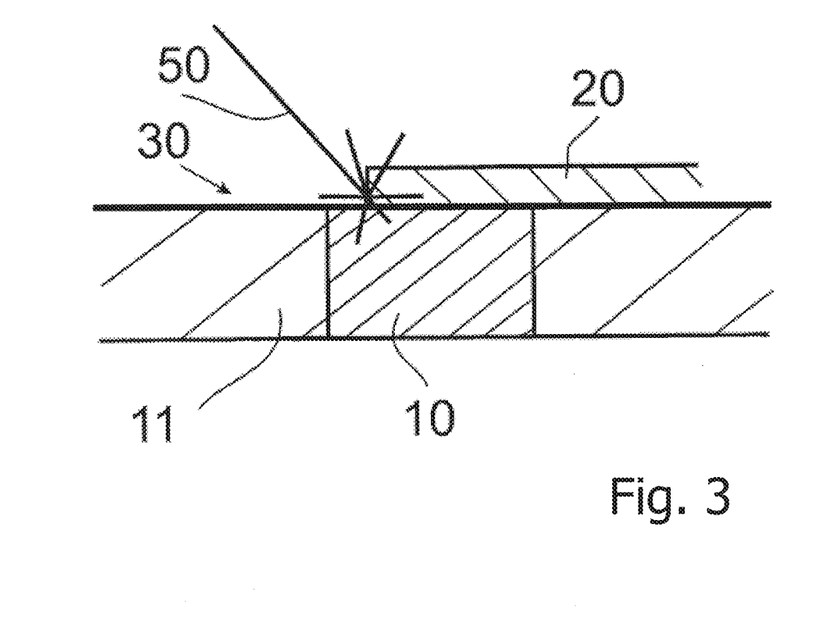
FIG. 3 illustrates an embodiment of connecting a wire to a pathway.

FIG. 3 illustrates a second way of generating a joint microstructure including the material of the wire 20 and the material of the pathway 10. Here a laser beam 50 is indicated as a means for heating the material of both the pathway 10 and the wire 20. A laser may supply a large amount of energy in a very short time so that in particular the material close to the outer surface may be heated.

In accordance with an embodiment, it might be of interest to further heat the material of the pathway 10 and not the material of the wire 20. In such a case, a heating of the materials may be performed in a two-step procedure, with firstly heating only the pathway 10 and secondly heating both the pathway 10 and the wire 20. It will be understood that the wire 20 may thus be arranged in contact with the pathway 10 after that pathway has been heated in the first heating step.

Figure 4:
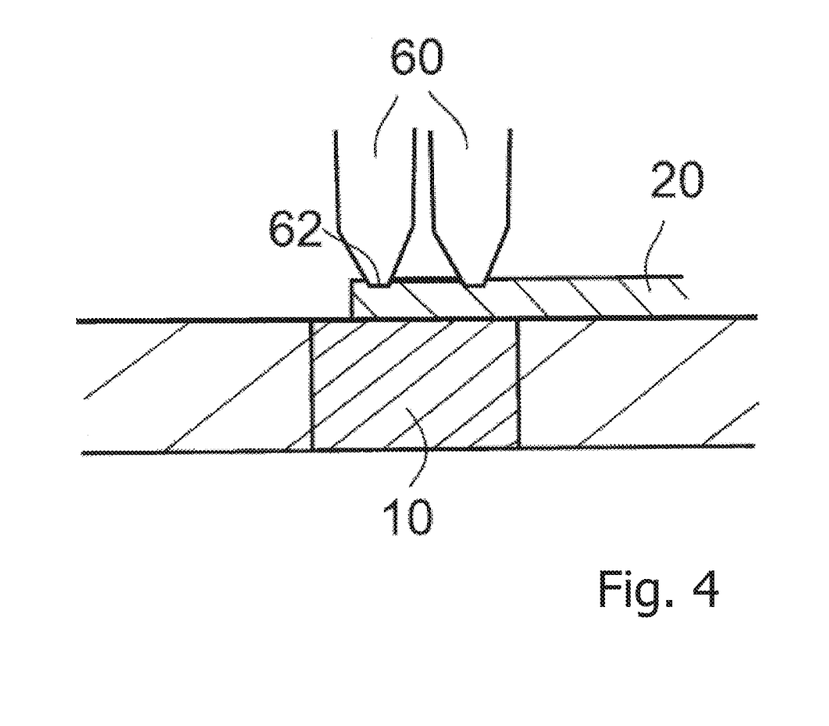
FIG. 4 illustrates an embodiment of connecting a wire to a pathway.

FIG. 4 illustrates a third way of generating a joint microstructure including the material of the wire 20 and the material of the pathway 10. Here, the respective end faces 62 of two electrodes 60 of a resistance welding tool are brought in contact with the wire 20, in an area above the pathway 10. A high current may then flow from the first one of the electrodes through the wire 20 and also the electrically conductive material of the pathway 10 and into the second one of the electrodes 60. The electrical resistance in that path causes the wire 20 and the pathway 10 to be heated up to a temperature at which both partially melt and, therefore, bond together.

Figure 5:
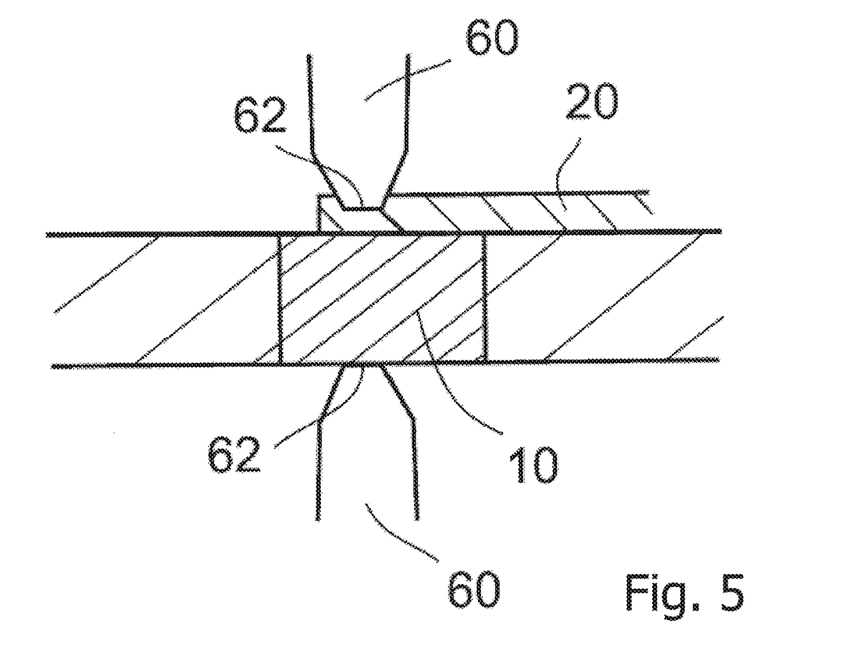
FIG. 5 illustrates an embodiment of connecting a wire to a pathway.

An alternative way of utilizing resistance welding is illustrated in FIG. 5. Here, the electrodes 60 of the resistance welding tool are arranged in contact to the wire 20 at a top surface of the pathway 10 and in contact with a bottom surface of the pathway 10 so that the current may flow completely through the pathway 10, as well as through the wire 20 for heating both.

Figure 6:
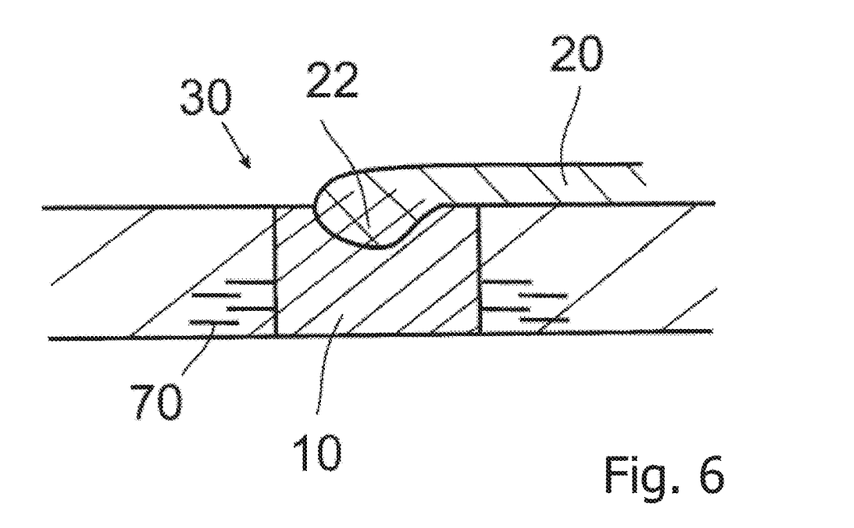
FIG. 6 illustrates a wire connected to a pathway.

A result of the heating by the described ways is illustrated in FIG. 6. Here, the end of the wire 20 is melted together with the material of the pathway 10. As indicated by the hatchings, the end portion 22 of the wire 20 now includes a combination of the material of the wire 20 (hatching from top left to bottom right) and at least the metallic material of the pathway 10 (hatching from bottom left to top right).

Further illustrated in FIG. 6 is a filter element 70 embedded in the feedthrough 30 in the vicinity of the pathway 10. The filter element 70 may be selected from the group consisting of: a high-pass filter, a low-pass filter, a band-pass filter. The filter element can be set up to subject electrical signals, which are conducted through the pathway 10, to a filtering, for example, a frequency filtering. The filter element 70 may, for example, be arranged on a side of the pathway 10 that faces the internal space (as illustrated in FIG. 6) and/or on a side that faces the external space. Designing filter elements by means of corresponding electrical elements, for example through at least one capacitor and at least one ohmic resistor and/or through an inductor and at least one ohmic resistor is basically known to the person skilled in the art. With regard to possible refinements of the filter elements, reference shall also be made to the above-mentioned references, for example, to U.S. Pat. No. 7,260,434.

It is noted that FIG. 6 may illustrate an end of a method for connecting an electrode to an implant.

Figure 7:
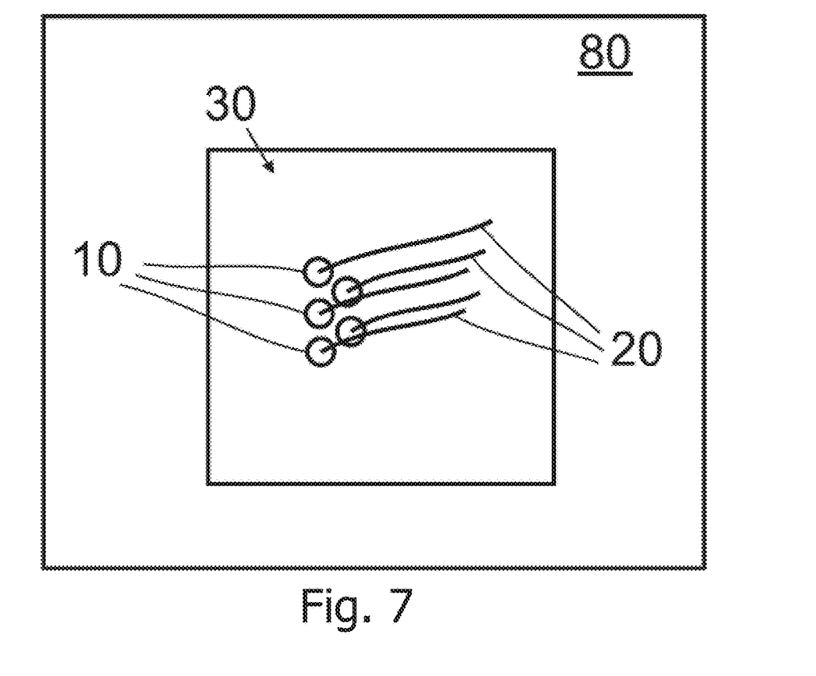
FIG. 7 illustrates an embodiment with a plurality of pathways.

Finally, FIG. 7 illustrates an embodiment having a plurality of pathways 10 to which a plurality of wire leads 20 are connected. Furthermore, FIG. 7 illustrates a ferrule 80, wherein that ferrule 80 may be made of a material which may differ from the insulating matrix of the feedthrough 30. The feedthrough 30 including the pathways 10 together with the ferrule(s) 80 may form the entire housing of the implant.

Although specific embodiments have been illustrated and described herein, it will be appreciated by those of ordinary skill in the art that a variety of alternate and/or equivalent implementations may be substituted for the specific embodiments illustrated and described without departing from the scope of the present invention. This application is intended to cover any adaptations or variations of the specific embodiments discussed herein. Therefore, it is intended that this invention be limited only by the claims and the equivalents thereof.

EXPERIMENTAL PART

Measurement Methods
Tensile Tests (Welded Samples)

The test was carried out using a BT1-FR2.5TN.D14 tensile tester obtained from Zwick GmbH & Co. KG, Ulm, Germany using Zwick testXpert II measuring software. The tensile tests were performed using a testing speed of 12.7 mm/min and the maximum force at which the wire and the cermet sample separated was determined. The wire was clamped by the upper clamping jaws and the cermet sample by the lower clamping jaws.

Conductivity

The conductivity was determined using an Agilent 34401A multimeter on samples having vias reaching through the sample. Wires having a length of 1.5 cm have been applied on each side of the same via by laser welding as outlined below and clamped using AGF1 miniature alligator clips available from Hirschmann. The resistance of the measurement assembly including clamps, wires and internal resistance of the multimeter was 0.023 Ohms and has been subtracted from the measured values in each experiment.

Used Materials
Cermet A

Ceramic foil made from $Al_2O_3$ and a binder further comprising vias of 0.4 mm diameter were subjected to a via filling process using a screen printer (EKRA Automatisierungssysteme GmbH, Bönnigheim, Germany) whereby the vias were filled with cermet paste A.

Cermet B

The above procedure for cermet A was repeated except that instead of cermet paste A cermet paste B was used.

Wires

The following wires have been used.

TABLE 1

| wire | diameter [μm] | tensile strength [MPa] | melting point [° C.] | heat conductivity [W/mK] |
|---|---|---|---|---|
| MP35N | 102 | 2167 | 1440 | 15 |
| Niob | 125 | 495 | 2469 | 52.3 |
| PtIr20 | 91.5 | 1408 | 1850 | 31 |
| Titan | 125 | 527 | 1670 | 16 |

Laser Welding

Prior to laser welding the wires were cleaned for 5 minutes using acetone in an ultrasonic bath.

The welding was performed under a protective atmosphere of argon. In order to prevent movement of the wire, the wires were fixed using Blu-Tack™ (available from Bostik) and, additionally, the wire was pressed to the surface of the cermet using a pincer.

Welding was accomplished using a Nd:YAG-laser adjusted manually using a height-adjustable probehead and an ocular. The applied voltage, time and the resulting applied energy are given in Table 2 below.

In case of cermet A the via as such was pretreated for 5 ms and 200 V using the Nd:YAG-laser whereby the laser was centered on the via. Thereby the cermet partially melts and a phase separation takes place, leading to a platinum droplet at the surface of the via leading to better tensile strength of the attached wire. In case of cermet B the pretreatment was not required due to the higher platinum content thereof.

Figure 8:
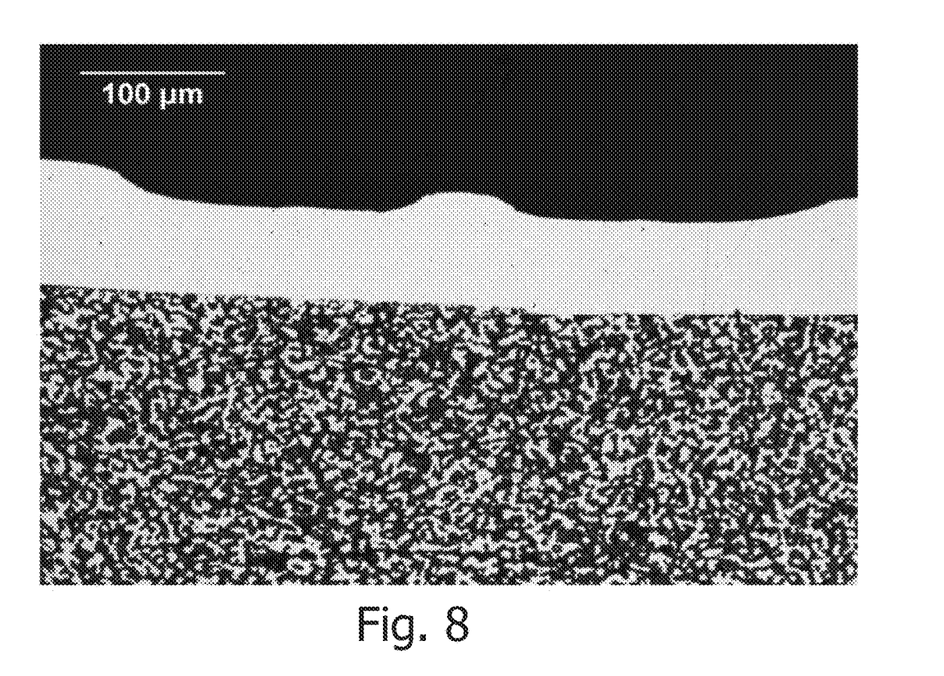
FIG. 8 illustrates a microscopic image of a PtIr wire attached by resistance-welding to a cermet A.

FIG. 8 illustrates a microscopic image of a PtIr wire attached by resistance-welding to cermet A.

The results are given in table 2 below.

TABLE 2

| cermet | wire | voltage [V] | time [ms] | energy [J] | tensile strength [MPa] | resistance cermet & wire[1] [Ohm] |
|---|---|---|---|---|---|---|
| A | MP35N | 195 | 8 | 4.68 | 564 | 7.89 |
| A | Niob | 195 | 7 | 4.05 | 339 | 1.12 |
| A | PtIr20 | 200 | 4 | 2.5 | 603 | 1.09 |
| A | Titan | 195 | 5 | 2.8 | 360 | 0.96 |
| B | MP35N | 215 | 6 | 5.33 | 1116 | 3.77 |
| B | Niob | 215 | 10 | 8.95 | 288 | 0.74 |
| B | PtIr20 | 215 | 10 | 8.95 | 630 | 1.04 |
| B | Titan | 215 | 6 | 5.33 | 527 | 1.16 |

[1] total length of the attached wires 3.0 cm, a major fraction of the resistance stems from the resistances of the wires and the contact resistances of the clamps to the wires.
[2] length 3.0 cm Wire Bonding
Cermet B Cermet B was prepared as above, whereby the vias have a diameter of 0.8 mm. Gold wires having a diameter of 32 μm were bonded via Ball-Wedge-bonding using a KNS capillary (Cu-FA-1157-P37, size 35.5 μm, CD 48.26, tip size 132 μm) by thermosonic bonding onto the vias of cermet B. The substrate was heated to 200° C. and a surface pressure of 35 g was applied. Three wires were attached on each of the vias.

The results of the tests are given in table 3 below.

TABLE 3

| test type | tensile modulus [MPa] (normalized to cross-section) |
|---|---|
| shear | 472 |
| ball test | 149 |
| wedge test | 119 |

What is claimed is:
1. A feedthrough system comprising:
   a feedthrough, a wire, and an electrode outside the feedthrough, all introduced into a human or animal body;
   wherein the feedthrough comprises an insulator and an electrically conductive cermet pathway;
   wherein the cermet pathway comprises an electrically conductive metallic material;

wherein the wire is arranged between the electrode and the cermet pathway;

wherein the wire is at least partially connected to the cermet pathway so that the material of the wire forms a joint microstructure with the electrically conductive material in the cermet pathway such that the material of the cermet pathway and the material of the wire are at least partially mixed with each other, the joint microstructure characterized by the absence of an intervening conductive material between the material of the wire and the electrically conductive material in the cermet pathway;

wherein the wire comprises a material selected from a group consisting of a platinum-iridium alloy and a nickel-cobalt-chromium alloy; and wherein the connection between the wire and the cermet pathway shows a tensile strength between 500 MPa and 1500 MPa.

2. The feedthrough system of claim 1, wherein the matrix of the material in the at least one area forming an electrically conductive cermet pathway comprises 30 to 90 percent by volume of a metal out of the group consisting of platinum, a platinum alloy, iridium, niobium, molybdenum, titanium, a titanium alloy, cobalt, zirconium, chromium, tantalum, a tantalum alloy, tungsten, a tungsten alloy.

3. The feedthrough system of claim 1, wherein the area forming the electrically conductive cermet pathway has a cross-sectional diameter of up to 5 mm.

4. The feedthrough system of claim 1, wherein the feedthrough comprises a plurality of electrically conductive cermet pathways, and wherein the wire comprises a plurality of wire leads, wherein different leads are connected to different cermet pathways, respectively.

5. The feedthrough system of claim 1, wherein the joint microstructure consists exclusively of the electrically conductive metallic material of the cermet pathway and of the material of the wire, and characterized by the absence of a solder.

6. An implantable medical device comprising:
a feedthrough, a wire, and an electrode outside the feedthrough all introduced into a human or animal body;
wherein the feedthrough comprises an insulator and an electrically conductive cermet pathway;
wherein the cermet pathway comprises an electrically conductive metallic material;
wherein the wire is arranged between the electrode and the cermet pathway; and
wherein the wire is at least partially connected to the cermet pathway so that the material of the wire forms a joint microstructure with the electrically conductive material in the cermet pathway such that the material of the cermet pathway and the material of the wire are at least partially mixed with each other, the joint microstructure characterized by the absence of an intervening conductive material between the material of the wire and the electrically conductive material in the cermet pathway;
an electronic device arranged at least partially in electrical contact with the feedthrough and;
wherein the wire comprises a material selected from a group consisting of a platinum-iridium alloy and a nickel-cobalt-chromium alloy;
wherein the connection between the wire and the cermet pathway shows a tensile strength between 500 MPa and 1500 MPa.

7. The implantable medical device of claim 6, wherein the matrix of the material in the at least one area forming an electrically conductive cermet pathway comprises 30 to 90 percent by volume of a metal out of the group consisting of platinum, a platinum alloy, iridium, niobium, molybdenum, titanium, a titanium alloy, cobalt, zirconium, chromium, tantalum, a tantalum alloy, tungsten, a tungsten alloy.

8. The implantable medical device of claim 6, wherein the area forming the electrically conductive cermet pathway has a cross-sectional diameter of up to 5 mm.

* * * * *